US011332581B2

(12) United States Patent
Gubbels et al.

(10) Patent No.: US 11,332,581 B2
(45) Date of Patent: May 17, 2022

(54) ELASTOMERIC COMPOSITIONS AND THEIR APPLICATIONS

(71) Applicant: DOW SILICONES CORPORATION, Midland, MI (US)

(72) Inventors: Frederic Gubbels, Houtain-le-Val (BE); Sandrine Teixeira de Carvalho, Obaix (BE)

(73) Assignee: DOW SILICONES CORPORATION, Midland, MI (US)

( * ) Notice: Subject to any disclaimer, the term of this patent is extended or adjusted under 35 U.S.C. 154(b) by 108 days.

(21) Appl. No.: 16/731,019

(22) Filed: Dec. 30, 2019

(65) Prior Publication Data

US 2020/0140617 A1  May 7, 2020

Related U.S. Application Data

(63) Continuation of application No. 15/546,164, filed as application No. PCT/EP2016/051573 on Jan. 26, 2016, now Pat. No. 10,563,015.

(30) Foreign Application Priority Data

Jan. 28, 2015 (GB) .................................. 1501430
Aug. 19, 2015 (GB) .................................. 1514689

(51) Int. Cl.
| | |
|---|---|
| C08G 77/16 | (2006.01) |
| C08G 77/08 | (2006.01) |
| H01L 23/29 | (2006.01) |
| C08K 5/5419 | (2006.01) |
| C09D 183/04 | (2006.01) |
| C08K 5/057 | (2006.01) |
| C09J 183/04 | (2006.01) |
| C08K 5/5415 | (2006.01) |
| A61K 47/34 | (2017.01) |
| A61L 15/26 | (2006.01) |
| A61L 24/04 | (2006.01) |
| C09D 183/06 | (2006.01) |
| C09J 183/06 | (2006.01) |
| C08G 77/18 | (2006.01) |
| H01L 31/048 | (2014.01) |
| H01L 33/56 | (2010.01) |

(52) U.S. Cl.
CPC .............. *C08G 77/08* (2013.01); *A61K 47/34* (2013.01); *A61L 15/26* (2013.01); *A61L 24/046* (2013.01); *C08G 77/16* (2013.01); *C08K 5/057* (2013.01); *C08K 5/5415* (2013.01); *C08K 5/5419* (2013.01); *C09D 183/04* (2013.01); *C09D 183/06* (2013.01); *C09J 183/04* (2013.01); *C09J 183/06* (2013.01); *H01L 23/296* (2013.01); *C08G 77/18* (2013.01); *H01L 31/0481* (2013.01); *H01L 33/56* (2013.01); *H01L 2924/0002* (2013.01)

(58) Field of Classification Search
CPC ........ C08G 77/50; C08G 77/18; C08G 77/16; C08G 77/12; C08G 77/20; C08L 101/10; B01J 21/00; B01J 23/40
See application file for complete search history.

(56) References Cited

U.S. PATENT DOCUMENTS

| | | | |
|---|---|---|---|
| 3,030,371 | A | 4/1962 | Walter |
| 3,334,067 | A | 8/1967 | Weyenberg |
| 3,419,516 | A | 12/1968 | Tarno |
| 4,087,585 | A | 5/1978 | Schulz |
| 4,754,013 | A | 6/1988 | Antonen |
| 4,908,140 | A | 3/1990 | Bausch et al. |
| 5,089,253 | A | 2/1992 | Halloran |
| 5,126,389 | A | 6/1992 | Ona et al. |
| 5,194,649 | A | 3/1993 | Okawa |
| 5,232,611 | A | 8/1993 | Ohashi et al. |

(Continued)

FOREIGN PATENT DOCUMENTS

| | | |
|---|---|---|
| CN | 1365379 A | 8/2002 |
| CN | 105440693 A | 3/2016 |

(Continued)

OTHER PUBLICATIONS

Lee, et al., 1970 Journal of Polymer Science Part A-2, Polymer Physics.
Michael A. Brook, Silicon in Organic, Organometallic and Polymer Chemistry, John Wiley & sons, Inc. (2000), pp. 285-287.
Mills, E., European Polymer Journal, 1969, vol. 5, pp. 675-695.
Noll, W.; Chemistry and Technology of Silicones, Academic Press Inc., New York, 1968, pp. 397-399.
O' Lenick, Jr., Basic Silicone Chemistry—A Review, Aug. 1999, Silicone Spectator, Jan. 2009.

(Continued)

*Primary Examiner* — Kuo Liang Peng
(74) *Attorney, Agent, or Firm* — Warner Norcross + Judd LLP

(57) ABSTRACT

A condensation curable gel composition is the disclosed. The composition comprises: (i) at least one condensation curable silyl terminated polymer having at least one hydrolysable and/or hydroxyl functional group(s) per molecule; (ii) a cross-linker selected from the group of a silicone, an organic polymer, a monosilane or a disilane molecule which contains at least two hydrolysable groups per molecule; and (iii) a condensation catalyst selected from the group of titanates, zirconates or tin (II). The molar ratio of hydroxyl and/or hydrolysable group(s) in polymer (i) to hydrolysable groups from component (ii) is between 0.5:1 and 1:1 using a monosilane cross-linker or 0.75:1 to 3:1 using disilanes. The titanates and zirconates comprise M-OR functions where M is titanium or zirconium and R is an aliphatic hydrocarbon group. The molar ratio of M-OR or tin (II) functions to the hydroxyl and/or hydrolysable groups in polymer (i) is comprised between 0.01:1 and 0.5:1.

14 Claims, No Drawings

(56) References Cited

U.S. PATENT DOCUMENTS

| | | |
|---|---|---|
| 5,262,088 A | 11/1993 | Hill et al. |
| 5,281,455 A | 1/1994 | Braun et al. |
| 5,300,171 A | 4/1994 | Braun et al. |
| 5,380,464 A | 1/1995 | McGee et al. |
| 5,684,110 A | 11/1997 | Kawamura |
| 5,804,631 A | 9/1998 | Mine et al. |
| 5,840,794 A | 11/1998 | Palmer |
| 6,015,784 A | 1/2000 | Kazuta et al. |
| 6,169,142 B1 | 1/2001 | Nakano et al. |
| 6,521,587 B1 | 2/2003 | L'Hostis et al. |
| 6,534,581 B1 | 3/2003 | Kleyer et al. |
| 6,593,413 B2 | 7/2003 | Muramatsu et al. |
| 6,642,309 B2 | 11/2003 | Komitsu et al. |
| 7,144,953 B2 | 12/2006 | Ueda et al. |
| 7,417,105 B2 | 8/2008 | Landon et al. |
| 7,893,170 B2 | 2/2011 | Wakioka et al. |
| 7,951,458 B2 | 5/2011 | Ogura et al. |
| 7,973,108 B2 | 7/2011 | Okamoto et al. |
| 8,030,371 B2 | 10/2011 | Chaussade |
| 8,231,944 B1 | 7/2012 | Schroeder |
| 8,536,109 B2 | 9/2013 | Delbrassinne et al. |
| 8,609,797 B2 | 12/2013 | Knepper et al. |
| 8,686,094 B2 | 4/2014 | Djurdjevic et al. |
| 8,785,537 B2 | 7/2014 | Carrard et al. |
| 8,801,890 B2 | 8/2014 | Verosky et al. |
| 9,051,435 B2 | 6/2015 | Takei et al. |
| 9,228,061 B2 | 1/2016 | Brandstadt et al. |
| 9,493,689 B2 | 11/2016 | Stanjek et al. |
| 9,527,985 B2 | 12/2016 | Okamatsu |
| 9,732,203 B2 | 8/2017 | Okamatsu |
| 10,150,888 B2 | 12/2018 | Simon et al. |
| 10,414,907 B2 | 9/2019 | Takahara |
| 10,563,015 B2 * | 2/2020 | Gubbels ............... C08K 5/5419 |
| 2002/0010251 A1 | 1/2002 | Muramatsu et al. |
| 2002/0193273 A1 | 12/2002 | Richards, III et al. |
| 2003/0119917 A1 | 6/2003 | Fey et al. |
| 2004/0002571 A1 | 1/2004 | Sakamoto et al. |
| 2006/0122295 A1 | 6/2006 | Oysaed et al. |
| 2006/0194067 A1 | 8/2006 | Beger et al. |
| 2006/0258818 A1 | 11/2006 | Kimura et al. |
| 2007/0173597 A1 | 7/2007 | Williams et al. |
| 2007/0219299 A1 | 9/2007 | Okamoto et al. |
| 2007/0237912 A1 | 10/2007 | Correia |
| 2007/0244249 A1 | 10/2007 | Correia |
| 2007/0282047 A1 | 12/2007 | Kimura et al. |
| 2007/0287780 A1 | 12/2007 | Wakabayashi et al. |
| 2008/0033087 A1 | 2/2008 | Okamoto et al. |
| 2008/0076878 A1 | 3/2008 | Wakioka et al. |
| 2008/0172807 A1 | 7/2008 | Brun |
| 2008/0179616 A1 | 7/2008 | Lee et al. |
| 2008/0194773 A1 | 8/2008 | Wakioka et al. |
| 2008/0279901 A1 | 11/2008 | Prigent et al. |
| 2008/0284106 A1 | 11/2008 | Maton et al. |
| 2008/0287636 A1 | 11/2008 | Wakabayashi et al. |
| 2008/0292572 A1 | 11/2008 | Benabdillah |
| 2008/0312365 A1 | 12/2008 | Maton et al. |
| 2008/0312366 A1 | 12/2008 | Maton et al. |
| 2008/0312367 A1 | 12/2008 | Maton et al. |
| 2008/0319152 A1 | 12/2008 | Okamoto et al. |
| 2009/0029043 A1 | 1/2009 | Rong et al. |
| 2009/0215944 A1 | 8/2009 | Maton et al. |
| 2009/0234052 A1 | 9/2009 | Maton et al. |
| 2010/0093598 A1 | 4/2010 | Davio et al. |
| 2010/0137454 A1 | 6/2010 | Barmes et al. |
| 2010/0144585 A1 | 6/2010 | Aksoy et al. |
| 2010/0184883 A1 | 7/2010 | Detemmerman et al. |
| 2011/0003081 A1 | 1/2011 | Maton et al. |
| 2011/0028646 A1 | 2/2011 | Sixt et al. |
| 2011/0144246 A1 | 6/2011 | Dabbous et al. |
| 2011/0165206 A1 | 7/2011 | Liu et al. |
| 2011/0248314 A1 | 10/2011 | Takei et al. |
| 2012/0016063 A1 | 1/2012 | Maton et al. |
| 2012/0022209 A1 | 1/2012 | Djurdjevic et al. |
| 2012/0022210 A1 | 1/2012 | Davio et al. |
| 2012/0123537 A1 | 5/2012 | Manesis et al. |
| 2012/0214902 A1 | 8/2012 | Detemmerman et al. |
| 2012/0214925 A1 | 8/2012 | Gubbels et al. |
| 2013/0338289 A1 | 12/2013 | Jadot et al. |
| 2014/0024731 A1 | 1/2014 | Blanc et al. |
| 2014/0235812 A1 | 8/2014 | Brandstadt et al. |
| 2014/0238471 A1 | 8/2014 | Wakita et al. |
| 2014/0256539 A1 * | 9/2014 | Takei ............... C08G 77/08 502/170 |
| 2014/0350176 A1 | 11/2014 | Fisher et al. |
| 2014/0364515 A1 | 12/2014 | Zeng et al. |
| 2015/0007938 A1 | 1/2015 | Stanjek et al. |
| 2015/0166859 A1 | 6/2015 | Choffat et al. |
| 2015/0183951 A1 | 7/2015 | Bhagwagar et al. |
| 2015/0224036 A1 | 8/2015 | Hasegawa |
| 2015/0257988 A1 | 9/2015 | Hasegawa |
| 2015/0315437 A1 | 11/2015 | Albaugh et al. |
| 2016/0009883 A1 | 1/2016 | Pernot |
| 2016/0326415 A1 | 11/2016 | Jadot et al. |
| 2017/0002201 A1 | 1/2017 | Von Malotki et al. |
| 2018/0009951 A1 | 1/2018 | Gubbels et al. |
| 2018/0237720 A1 | 8/2018 | Barnes et al. |
| 2019/0177486 A1 | 6/2019 | Baily et al. |
| 2019/0177584 A1 | 6/2019 | Gubbels et al. |
| 2019/0291024 A1 | 9/2019 | Rahma et al. |
| 2019/0338077 A1 | 11/2019 | Chambard et al. |
| 2020/0140617 A1 | 5/2020 | Gubbels et al. |
| 2020/0190324 A1 | 6/2020 | Gubbels |
| 2020/0392431 A1 | 12/2020 | Ugazio et al. |
| 2020/0398537 A1 | 12/2020 | Gubbels et al. |
| 2020/0399514 A1 | 12/2020 | Gubbels et al. |

FOREIGN PATENT DOCUMENTS

| | | |
|---|---|---|
| CN | 105505297 A | 4/2016 |
| EP | 217501 A2 | 4/1987 |
| EP | 341952 A2 | 11/1989 |
| EP | 356210 A2 | 2/1990 |
| EP | 393511 A2 | 10/1990 |
| EP | 539234 A2 | 4/1993 |
| EP | 0539234 B1 | 3/1997 |
| EP | 2221328 A2 | 8/2010 |
| EP | 2221329 A1 | 8/2010 |
| EP | 2792690 A1 | 10/2014 |
| GB | 2424898 A | 10/2006 |
| JP | S5269460 A | 12/1978 |
| JP | H05125284 A | 5/1993 |
| JP | H08269331 A | 10/1996 |
| JP | H08302193 A | 11/1996 |
| JP | H0912892 A | 1/1997 |
| JP | 2000178448 A | 6/2000 |
| JP | 2000281523 A | 10/2000 |
| JP | 2001200161 A | 7/2001 |
| JP | 2002205911 A | 7/2002 |
| JP | 2002235004 A | 8/2002 |
| JP | 2003226812 A | 8/2003 |
| JP | 2006342327 A | 12/2006 |
| JP | 2007119695 A | 5/2007 |
| JP | 2008174554 A | 7/2008 |
| JP | 2010248446 A | 11/2010 |
| JP | 2011137119 A | 7/2011 |
| JP | 2012251058 A | 12/2012 |
| JP | 5180140 B2 | 4/2013 |
| JP | 2013234245 A | 11/2013 |
| JP | 5621211 B2 | 11/2014 |
| JP | 2016128497 A | 7/2016 |
| KR | 960007223 B1 | 5/1996 |
| KR | 20020009424 A | 2/2002 |
| WO | 2001042365 A1 | 6/2001 |
| WO | 2001096463 A1 | 12/2001 |
| WO | 2005108499 A1 | 11/2005 |
| WO | 2007117551 A1 | 10/2007 |
| WO | 2007117552 A1 | 10/2007 |
| WO | 2008045395 A2 | 4/2008 |
| WO | 2008045417 A2 | 4/2008 |
| WO | 2008045427 A1 | 4/2008 |
| WO | 2009013309 A1 | 1/2009 |
| WO | 2009128883 A1 | 10/2009 |
| WO | 2010071092 | * 6/2010 |
| WO | 2010071092 A1 | 6/2010 |

(56) References Cited

FOREIGN PATENT DOCUMENTS

| | | |
|---|---|---|
| WO | 2010115782 A2 | 10/2010 |
| WO | 2010117744 A2 | 10/2010 |
| WO | 2010143357 A1 | 12/2010 |
| WO | 2013036548 A3 | 3/2013 |
| WO | 2013100175 A1 | 7/2013 |
| WO | 2014022377 A1 | 2/2014 |
| WO | 2016120270 A1 | 8/2016 |
| WO | 2017030128 A1 | 2/2017 |
| WO | 2017191322 A1 | 11/2017 |
| WO | 2018024856 A1 | 2/2018 |
| WO | 2018024857 A1 | 2/2018 |
| WO | 2018024858 A1 | 2/2018 |
| WO | 2018024859 A1 | 2/2018 |
| WO | 2018024860 A1 | 2/2018 |
| WO | 2018024865 A1 | 2/2018 |
| WO | 2018050503 A1 | 3/2018 |
| WO | 2018200796 A1 | 11/2018 |

OTHER PUBLICATIONS

International Search Report for Application No. PCT/EP2017/069743, dated Nov. 14, 2017, 3 pages.
International Search Report for Application No. PCT/EP2017/069744, dated Nov. 9, 2017, 3 pages.
International Search Report for Application No. PCT/EP2017/069745, dated Nov. 9, 2017, 3 pages.
International Search Report for Application No. PCT/EP2017/069746, dated Oct. 30, 2017, 4 pages.
International Search Report for Application No. PCT/EP2017/069748, dated Sep. 27, 2017, 4 pages.
International Search Report for Application No. PCT/EP2017/069749, dated Oct. 30, 2017, 4 pages.
International Search Report for Application No. PCT/EP2017/069753, dated Nov. 14, 2017, 3 pages.
Machine assisted English translation of CN105440693A obtained from https://patents.google.com/patent on Mar. 8, 2021, 6 pages.
Machine assisted English translation of CN105505297A obtained from https://patents.google.com/patent on Mar. 8, 2021, 10 pages.
Machine assisted English translation of CN1365379A obtained from https://patents.google.com/patent on Mar. 8, 2021, 12 pages.
Machine assisted English translation of JP5180140B2 obtained from https://patents.google.com/patent on Mar. 8, 2021, 10 pages.
Machine assisted English translation of JP5621211B2 obtained from https://patents.google.com/patent on Mar. 8, 2021, 10 pages.
Machine assisted English translation of JPS5269460A obtained from https://worldwide.espacenet.com/patent on Mar. 8, 2021, 10 pages.
Machine assisted English translation of JP2000178448A obtained from https://worldwide.espacenet.com/patent on Mar. 9, 2021, 8 pages.
Machine assisted English translation of JP2000281523A obtained from https://worldwide.espacenet.com/patent on Mar. 9, 2021, 19 pages.
Machine assisted English translation of JP2001200161A obtained from https://patents.google.com/patent on Mar. 8, 2021, 7 pages.
Machine assisted English translation of JP2002205911A obtained from https://patents.google.com/patent on Mar. 9, 2021, 10 pages.
Machine assisted English translation of JP2002235004A obtained from https://patents.google.com/patent on Mar. 9, 2021, 10 pages.
Machine assisted English translation of JP2003226812A obtained from https://patents.google.com/patent on Mar. 9, 2021, 13 pages.
Machine assisted English translation of JP2006342327A obtained from https://patents.google.com/patent on Mar. 8, 2021, 9 pages.
Machine assisted English translation of JP2007119695A obtained from https://patents.google.com/patent on Mar. 8, 2021, 9 pages.
Machine assisted English translation of JP2008174554A obtained from https://patents.google.com/patent on Mar. 9, 2021, 18 pages.
Machine assisted English translation of JP2012251058A obtained from https://patents.google.com/patent on Mar. 8, 2021, 16 pages.
Machine assisted English translation of JP2013234245A obtained from https://patents.google.com/patent on Mar. 8, 2021, 8 pages.
Machine assisted English translation of JP2016128497A obtained from https://patents.google.com/patent on Mar. 9, 2021, 15 pages.
Machine assisted English translation of WO2017030128A1 obtained from https://patents.google.com/patent on Mar. 8, 2021, 18 pages.
International Search Report for PCT/EP2016/051573 dated Mar. 11, 2016, 3 pages.
Machine assisted English translation of JPH08302193A obtained from https://patents.google.com/patent on Mar. 30, 2020, 8 pages.
Machine assisted English translation of JPH08269331A obtained from https://patents.google.com/patent on Mar. 30, 2020, 8 pages.
Machine assisted English translation of JP2010248446A obtained from https://patents.google.com/patent on Mar. 30, 2020, 11 pages.
Machine assisted English translation of JP2011137119A obtained from https://patents.google.com/patent on Mar. 30, 2020, 14 pages.
Machine assisted English translation of WO2010143357A1 obtained from https://patents.google.com/patent on Mar. 30, 2020, 25 pages.

* cited by examiner

ELASTOMERIC COMPOSITIONS AND THEIR APPLICATIONS

CROSS-REFERENCE TO RELATED APPLICATIONS

This application is a Continuation of National Stage patent application Ser. No. 15/546,164 filed on 25 Jul. 2017, which claims priority to and all advantages of International Application No. PCT/EP2016/051573 filed on 26 Jan. 2016, which claims priority to and all advantages of GB Patent Application No. 1501430.1 filed on 28 Jan. 2015 and GB Patent Application No. 1514689.7 filed on 19 Aug. 2015, the contents of which are incorporated herein by reference.

The present disclosure generally relates to Silicone encapsulants and gels cured via a condensation cure chemistry and their applications.

In many instances gels used as coating, potting, and encapsulating materials must maintain adhesion to substrates and/or other materials. In electronics for example, gels are a special class of encapsulants that cure to form an extremely soft material. They are used to provide high levels of stress relief to sensitive circuitry. Gels perform many important functions in electronics. Their major job is to protect electronic assemblies and components from adverse environments by: functioning as dielectric insulation, protecting the circuit from moisture and other contaminants, relieving mechanical and thermal stress on components In such situations the gels are required to adhere to electronic and electrical components and printed circuit boards in addition to the electrical connectors and conductors that pass through the coating or encapsulating material.

The materials that form the gels are expensive being based on addition cure chemistry, i.e. they are cured by the reaction of a silicon hydride group with onto an unsaturated carbon radical with the help of a catalyst, which is typically a platinum based compound. Historically the industry has preferred addition cure compositions of this type for these applications because they immediately cure throughout the body of the compound resulting in a cured gel material in a matter of minutes whilst condensation cure systems are significantly slower, titanate cured condensation processes can take e.g. up to 7 days curing per 6 mm of depth of the body of the uncured material. Tin cured condensation systems do cure over a shorter period but they are not desired for e.g. electronics applications because undergo reversion (i.e. depolymerisation) at temperatures above 80° C.

Whilst from a cure speed standpoint gels made from these hydrosilylation cure compositions are excellent there are several potential problems and/or disadvantages with the use of these types of products. Firstly they are generally cured at elevated temperature (i.e. temperatures significantly above room temperature. The hydrosilylation compositions can be contaminated and rendered uncurable due to inactivation of expensive platinum based cure catalysts. The platinum catalysts are sensitive and may be poisoned by amine containing compounds, sulphur containing compounds and phosphorus containing compounds. It is well known to people skilled in the art that alkoxy titanium compounds—alkyl titanates—are suitable catalysts for formulating one component moisture curable silicones (References: Noll, W.; Chemistry and Technology of Silicones, Academic Press Inc., New York, 1968, p. 399, Michael A. Brook, silicon in organic, organometallic and polymer chemistry, John Wiley & sons, Inc. (2000), p. 285). Titanate catalysts have been widely described for their use to formulate one part curing silicone elastomer. To formulate multi component silicone elastomers other metal catalysts are used such as tin or zinc catalyst, e.g. dibutyl tin dilaurate, tin octoate, zinc octoate (Noll, W.; Chemistry and Technology of Silicones, Academic Press Inc., New York, 1968, p. 397). In two component silicones, one part contains a filler which typically will contain the moisture required to activate the condensation cure in the bulk of the product. In the presence of such an amount of moisture, alkyltitanate catalysts are fully hydrolysed to form tetrahydroxy titanate, which is insoluble in silicone and loses its catalytic efficiency.

There is provided a gel which is the condensation reaction product of:
  (i) at least one condensation curable silyl terminated polymer having at least one, typically at least 2 hydrolysable and/or hydroxyl functional groups per molecule;
  (ii) a cross-linker selected from the group of a silicone, an organic polymer, a silane or a disilane molecule which contains at least two hydrolysable groups per molecule and typically at least three hydrolysable groups per molecule and
  (iii) a condensation catalyst selected from the group of titanates, zirconates or tin II characterized in that the molar ratio of hydroxyl and/or hydrolysable groups in polymer (i) to hydrolysable groups from (ii) is between 0.5:1 to 1:1 using a monosilane cross linker or 0.75:1 to 3:1 using disilanes and the molar ratio of M-OR or tin (II) functions to the hydroxyl and/or hydrolysable groups in polymer (i) is comprised between 0.01:1 and 0.5:1, where M is titanium or zirconium.

The present invention describes a condensation curable gel composition based on titanate/zirconate or tin (II) cure catalysts that can be cured in the absence of moisture bearing filler leading to a bulk cure in a few minutes to a few hours depending on the composition. The condensation curable gel composition comprises:
  (i) at least one condensation curable silyl terminated polymer having at least one, typically at least 2 hydrolysable and/or hydroxyl functional groups per molecule;
  (ii) a cross-linker selected from the group of a silicone, an organic polymer, a silane or a disilane molecule which contains at least two hydrolysable groups per molecule and typically at least three hydrolysable groups per molecule and
  (iii) a condensation catalyst selected from the group of titanates, zirconates or tin (II) characterized in that the molar ratio of hydroxyl and/or hydrolysable groups in polymer (i) to hydrolysable groups from (ii) is between 0.5:1 and 1:1 using a monosilane cross linker or 0.75:1 to 3:1 using disilanes and the molar ratio of M-OR or tin II functions to the hydroxyl and/or hydrolysable groups in polymer (i) is comprised between 0.01:1 and 0.5:1, where M is titanium or zirconium.

The current invention is describing a condensation curing silicone elastomer (gel) exhibiting a hardness below Shore 80 in the type 00 scale according to ASTM D 2240-05 (2010). Products having a hardness of Shore below 0 in the 00 scale, i.e. soft gels can also be obtained using compositions claimed in this invention. The hardness of such gels are typically measured with the help of a penetrometer.

The main advantages of these compositions are to cure at room temperature, to be more resistant to contaminants than platinum cure silicones Polymer (i) is at least one or alternatively a moisture/condensation curable silyl terminated polymer. Any suitable moisture/condensation curable silyl terminated polymer may be utilised including polydialkyl siloxanes, alkylphenyl siloxane, or organic based polymers with silyl terminal groups e.g. silyl polyethers, silyl acrylates and silyl terminated polyisobutylenes or copolymers of any of the above. Preferably the polymer is a polysiloxane based polymer containing at least two hydroxyl or hydrolysable groups, most preferably the polymer comprises terminal hydroxyl or hydrolysable groups. Examples of suitable hydroxyl or hydrolysable groups include —Si(OH)$_3$, —(R$^a$)Si(OH)$_2$, —(R$^a$)$_2$Si(OH), —R$^a$Si(OR$^b$)$_2$, —Si(OR$^b$)$_3$, —R$^a{}_2$SiOR$^b$ or —(R$^a$)$_2$ Si—R$^c$—SiR$^d{}_p$(OR$^b$)$_{3-p}$ where each R$^a$ independently represents a monovalent hydrocarbyl group, for example, an alkyl group, in particular having from 1 to 8 carbon atoms, (and is preferably methyl); each R$^b$ and R$^d$ group is independently an alkyl or alkoxy group in which the alkyl groups suitably have up to 6 carbon atoms; R$^c$ is a divalent hydrocarbon group which may be interrupted by one or more siloxane spacers having up to six silicon atoms; and p has the value 0, 1 or 2.

Preferably polymer (i) has the general formula $$X^3\text{-}A\text{-}X^1 \quad (1)$$

where X$^3$ and X$^1$ are independently selected from siloxane groups which terminate in hydroxyl or hydrolysable groups and A is a siloxane containing polymeric chain.

Examples of hydroxyl-terminating or hydrolysable groups X$^3$ or X$^1$ include —Si(OH)$_3$, —(R$^a$)Si(OH)$_2$, —(R$^a$)$_2$ Si(OH), —(R$^a$)Si(OR$^b$)$_2$, —Si(OR$^b$)$_3$, —(R$^a$)$_2$Si-OR$^b$ or —(R$^a$)$_2$Si—R$^c$—Si(R$^d$)$_p$(OR$^b$)$_{3-p}$ as defined above with each R$^b$ group, when present, typically being a methyl group. Preferably the X$^3$ and/or X$^1$ terminal groups are hydroxydialkyl silyl groups, e.g. hydroxydimethyl silyl groups or alkoxydialkyl silyl groups e.g. methoxydimethyl silyl or ethoxydimethyl silyl.

Examples of suitable siloxane groups in polymeric chain A of formula (I) are those which comprise a polydiorganosiloxane chain. Thus polymeric chain A preferably includes siloxane units of formula (2)

$$-(R^5{}_s SiO_{(4-s)/2})- \quad (2)$$

in which each R$^5$ is independently an organic group such as a hydrocarbyl group having from 1 to 10 carbon atoms optionally substituted with one or more halogen group such as chlorine or fluorine and s is 0, 1 or 2. Particular examples of groups R$^5$ include methyl, ethyl, propyl, butyl, vinyl, cyclohexyl, phenyl, tolyl group, a propyl group substituted with chlorine or fluorine such as 3,3,3-trifluoropropyl, chlorophenyl, beta-(perfluorobutyl)ethyl or chlorocyclohexyl group. Suitably, at least some and preferably substantially all of the groups R$^5$ are methyl.

Typically the polymers of the above type will have a viscosity in the order of 1000 to 300,000 mPa·s, alternatively 1000 to 100,000 mPa·s at 25° C. measured by using a Brookfield cone plate viscometer (RV DIII) using a cone plate.

Preferred polysiloxanes containing units of formula (2) are thus polydiorganosiloxanes having terminal, silicon-bound hydroxyl groups or terminal, silicon-bound organic radicals which can be hydrolysed using moisture as defined above. The polydiorganosiloxanes may be homopolymers or copolymers. Mixtures of different polydiorganosiloxanes having terminal condensable groups are also suitable.

In accordance with the present invention polymeric chain A may alternatively be organic based polymers with silyl terminal groups e.g. silyl polyethers, silyl acrylates and silyl terminated polyisobutylenes. In the case of silyl polyethers the polymer chain is based on polyoxyalkylene based units. Such polyoxyalkylene units preferably comprise a linear predominantly oxyalkylene polymer comprised of recurring oxyalkylene units, (—C$_n$H$_{2n}$—O—) illustrated by the average formula (—C$_n$H$_{2n}$—O—)$_y$ wherein n is an integer from 2 to 4 inclusive and y is an integer of at least four. The average molecular weight of each polyoxyalkylene polymer block may range from about 300 to about 10,000, but can be higher in molecular weight. Moreover, the oxyalkylene units are not necessarily identical throughout the polyoxyalkylene monomer, but can differ from unit to unit. A polyoxyalkylene block, for example, can be comprised of oxyethylene units, (—C$_2$H$_4$—O—); oxypropylene units (—C$_3$H$_6$—O—); or oxybutylene units, (—C$_4$H$_8$—O—); or mixtures thereof.

Other polyoxyalkylene units may include for example: units of the structure $$-[-R^e-O-(-R^f-O-)_p-Pn\text{-}CR^g{}_2\text{-}Pn\text{-}O-(-R^f-O-)_q-R^e]-$$

in which Pn is a 1,4-phenylene group, each R$^e$ is the same or different and is a divalent hydrocarbon group having 2 to 8 carbon atoms, each R$^f$ is the same or different and, is, an ethylene group or propylene group, each R$^g$ is the same or different and is, a hydrogen atom or methyl group and each of the subscripts p and q is a positive integer in the range from 3 to 30.

For the purpose of this application "Substituted" means one or more hydrogen atoms in a hydrocarbon group has been replaced with another substituent. Examples of such substituents include, but are not limited to, halogen atoms such as chlorine, fluorine, bromine, and iodine; halogen atom containing groups such as chloromethyl, perfluorobutyl, trifluoroethyl, and nonafluorohexyl; oxygen atoms; oxygen atom containing groups such as (meth)acrylic and carboxyl; nitrogen atoms; nitrogen atom containing groups such as amino-functional groups, amido-functional groups, and cyano-functional groups; sulphur atoms; and sulphur atom containing groups such as mercapto groups.

The backbone of the organic polymer (A) which may contain organic leaving groups within the molecule used in the present invention is not particularly limited and may be any of organic polymers having various backbones. The backbone preferably includes at least one selected from a hydrogen atom, a carbon atom, a nitrogen atom, an oxygen atom, and a sulphur atom because the resulting composition has excellent curability and adhesion.

Crosslinkers that can be used are generally moisture curing silanes. For the sake of the disclosure herein a monosilane cross-linker shall be understood to mean a molecule containing a single silyl functional group, which contains at least one hydrolysable group. For the sake of the disclosure herein a disilane means a molecule containing two silyl groups, each containing at least one hydrolysable group. Typically, a cross-linker requires a minimum of 2 hydrolysable groups per molecule and preferably 3 or more. In both case the molecule can be polymeric.

Any suitable cross-linker may be used for example alkoxy functional silanes, oximosilanes, acetoxy silanes, acetonoxime silanes, enoxy silanes. For softer materials disilanes are preferable. The crosslinker used in the moisture curable composition as hereinbefore described is preferably a silane compound containing hydrolysable groups. These include one or more silanes or siloxanes which contain silicon bonded hydrolysable groups such as acyloxy groups (for example, acetoxy, octanoyloxy, and benzoyloxy groups); ketoximino groups (for example dimethyl ketoximo, and isobutylketoximino); alkoxy groups (for example methoxy, ethoxy, and propoxy) and alkenyloxy groups (for example isopropenyloxy and 1-ethyl-2-methylvinyloxy).

Alternatively, the crosslinker may have a siloxane or organic polymeric backbone. In the case of such siloxane or organic based cross-linkers the molecular structure can be straight chained, branched, cyclic or macromolecular. Suitable polymeric crosslinkers may have a similar polymeric backbone chemical structure to polymeric chain A as depicted in formula 1 above here above but typically any such crosslinkers ii utilised will be of significantly shorter chain length than polymer i.

The crosslinker may have two but preferably has three or four silicon-bonded condensable (preferably hydroxyl and/or hydrolysable) groups per molecule which are reactive with the condensable groups in organopolysiloxane polymer (a). In one embodiment the cross-linker used is a disilane having up to 6 hydroxyl and/or hydrolysable groups per molecule. When the crosslinker is a silane and when the silane has three silicon-bonded hydrolysable groups per molecule, the fourth group is suitably a non-hydrolysable silicon-bonded organic group. These silicon-bonded organic groups are suitably hydrocarbyl groups which are optionally substituted by halogen such as fluorine and chlorine. Examples of such fourth groups include alkyl groups (for example methyl, ethyl, propyl, and butyl); cycloalkyl groups (for example cyclopentyl and cyclohexyl); alkenyl groups (for example vinyl and allyl); aryl groups (for example phenyl, and tolyl); aralkyl groups (for example 2-phenylethyl) and groups obtained by replacing all or part of the hydrogen in the preceding organic groups with halogen. Preferably however, the fourth silicon-bonded organic groups is methyl.

Silanes and siloxanes which can be used as crosslinkers include alkyltrialkoxysilanes such as methyltrimethoxysilane (MTM) and methyltriethoxysilane, alkenyltrialkoxysilanes such as vinyltrimethoxysilane and vinyltriethoxysilane, isobutyltrimethoxysilane (iBTM). Other suitable silanes include ethyltrimethoxysilane, vinyltriethoxysilane, phenyltrimethoxysilane, alkoxytrioximosilane, alkenyltrioximosilane, 3,3,3-trifluoropropyltrimethoxysilane, methyltriacetoxysilane, vinyltriacetoxysilane, ethyl triacetoxysilane, di-butoxy diacetoxysilane, phenyltripropionoxysilane, methyltris(methylethylketoximo) silane, vinyl-tris-methylethylketoximo)silane, methyltris (methylethylketoximino)silane, methyltris(isopropenoxy) silane, vinyltris(isopropenoxy)silane, ethylpolysilicate, n-propylorthosilicate, ethylorthosilicate, dimethyltetraacetoxydisiloxane. The cross-linker used may also comprise any combination of two or more of the above. The cross-linker may be polymeric, with a silicone or organic polymer chain bearing alkoxy functional end groups such as 1,6-bis (trimethoxysilyl)hexane (alternatively known as hexamethoxydisilylhexane). The molar ratio of hydroxyl and/or hydrolysable groups in polymer (i) to hydrolysable groups from (ii) is between 0.5:1 to 1:1 using a monosilane cross linker or 0.75:1 to 3:1, alternatively 0.75:1 to 1.5:1 using disilanes.

The composition further comprises a condensation catalyst. This increases the speed at which the composition cures. The catalyst chosen for inclusion in a particular silicone sealant composition depends upon the speed of cure required. Titanate and/or zirconate based catalysts may comprise a compound according to the general formula Ti[OR$^{22}$]$_4$ where each R$^{22}$ may be the same or different and represents a monovalent, primary, secondary or tertiary aliphatic hydrocarbon group which may be linear or branched containing from 1 to 10 carbon atoms. Optionally the titanate may contain partially unsaturated groups. However, preferred examples of R$^{22}$ include but are not restricted to methyl, ethyl, propyl, isopropyl, butyl, tertiary butyl and a branched secondary alkyl group such as 2,4-dimethyl-3-pentyl. Preferably, when each R$^{22}$ is the same, R$^{22}$ is an isopropyl, branched secondary alkyl group or a tertiary alkyl group, in particular, tertiary butyl. Suitable examples include for the sake of example, tetra n-butyl titanate, tetra t-butyl titanate, tetra t-butoxy titanate, tetraisopropoxy titanate and diisopropoxydiethylacetoacetate titanate. Alternatively, the titanate may be chelated. The chelation may be with any suitable chelating agent such as an alkyl acetylacetonate such as methyl or ethylacetylacetonate. Alternatively, the titanate may be monoalkoxy titanates bearing three chelating agents such as for example 2-propanolato, tris isooctadecanoato titanate. The molar ratio of M-OR or tin (II) functions to the hydroxyl and/or hydrolysable groups in polymer (i) is comprised between 0.01:1 and 0.5:1, where M is titanium or zirconium.

The gel as hereinbefore described is typically made from the condensation curable gel composition which is stored in a 2 part manner. The two part compositions may be missed using any appropriate standard two-part mixing equipment with a dynamic or static mixer and is optionally dispensed therefrom for use in the application for which it is intended. In one embodiment in accordance with claim 1 or a condensation curable gel composition in accordance with claim 2 wherein the condensation curable gel composition is stored in two parts having polymer (i) and cross-linker (ii) in one part and polymer (i) and catalyst (iii) in the other part. In an alternative embodiment the condensation curable gel composition is stored in two parts having cross-linker (ii) in one part and polymer (i) and catalyst (iii) in the other part. In a still further embodiment the condensation curable gel composition is stored in two parts having a first polymer (i) and cross-linker (ii) in one part and a second polymer (i) and catalyst (iii) in the other part.

Fillers

Typically in the present invention the composition used does not contain a filler of any sort. In particular the composition does not contain fillers that brings a significant amount of moisture in the composition. The total moisture content brought about by the filler should not exceed 0.02% (which can be measured in accordance with ISO 787-2: 1981) of the total composition. Suitable anhydrous filler may be utilised if required.

Should the need arise the composition may incorporate anhydrous fillers, for example thermally and/or electrically conductive fillers e.g. metallic fillers, anhydrous inorganic fillers and anhydrous meltable fillers, or a combination thereof. Metallic fillers include particles of metals and particles of metals having layers on the surfaces of the particles. These layers may be, for example, metal nitride layers or metal oxide layers on the surfaces of the particles. Suitable metallic fillers are exemplified by particles of metals selected from the group consisting of aluminium, copper, gold, nickel, tin, silver, and combinations thereof, and alternatively aluminium. Suitable metallic fillers are further exemplified by particles of the metals listed above having layers on their surfaces selected from the group consisting of aluminium nitride, aluminium oxide, copper oxide, nickel oxide, silver oxide, and combinations thereof. For example, the metallic filler may comprise aluminium particles having aluminium oxide layers on their surfaces.

Inorganic fillers which are anhydrous and may be exemplified by onyx; aluminium trihydrate, metal oxides such as aluminium oxide, beryllium oxide, magnesium oxide, and zinc oxide; nitrides such as aluminium nitride and boron nitride; carbides such as silicon carbide and tungsten carbide; and combinations thereof. Further fillers may include barium titanate, carbon fibres, diamond, graphite, magnesium hydroxide, and a combination thereof.

Meltable fillers may comprise Bi, Ga, In, Sn, or an alloy thereof. The meltable filler may optionally further comprise Ag, Au, Cd, Cu, Pb, Sb, Zn, or a combination thereof. Examples of suitable meltable fillers include Ga, In—Bi—Sn alloys, Sn—In—Zn alloys, Sn—In—Ag alloys, Sn—Ag—Bi alloys, Sn—Bi—Cu—Ag alloys, Sn—Ag—Cu—Sb alloys, Sn—Ag—Cu alloys, Sn—Ag alloys, Sn—Ag—Cu—Zn alloys, and combinations thereof. The meltable filler may have a melting point ranging from 50° C. to 250° C., alternatively 150° C. to 225° C. The meltable filler may be a eutectic alloy, a non-eutectic alloy, or a pure metal. Meltable fillers are commercially available.

The shape of the thermally conductive filler particles is not specifically restricted, however, rounded or spherical particles may prevent viscosity increase to an undesirable level upon high loading of the thermally conductive filler in the composition. The average particle size of the thermally conductive filler will depend on various factors including the type of thermally conductive filler selected and the exact amount added to the curable composition, as well as the bondline thickness of the device in which the cured product of the composition will be used. In some particular instances, the thermally conductive filler may have an average particle size ranging from 0.1 micrometre to 80 micrometres, alternatively 0.1 micrometre to 50 micrometres, and alternatively 0.1 micrometre to 10 micrometres.

The thermally conductive filler may be a single thermally conductive filler or a combination of two or more thermally conductive fillers that differ in at least one property such as particle shape, average particle size, particle size distribution, and type of filler. In some embodiments, combinations of metallic and inorganic fillers, such as a combination of aluminium and aluminium oxide fillers; a combination of aluminium and zinc oxide fillers; or a combination of aluminium, aluminium oxide, and zinc oxide fillers may be used. In other embodiments, it may be desirable to combine a first conductive filler having a larger average particle size with a second conductive filler having a smaller average particle size in a proportion meeting the closest packing theory distribution curve. An example would be mixing two aluminium oxide preparations having different average particle sizes. In other embodiments, different thermally conductive filler materials with difference sizes may be used, for example, a combination of an aluminium oxide having a larger average particle size with a zinc oxide having a smaller average particle size. Alternatively, it may be desirable to use combinations of metallic fillers, such as a first aluminium having a larger average particle size and a second aluminium having a smaller average particle size. Use of a first filler having a larger average particle size and a second filler having a smaller average particle size than the first filler may improve packing efficiency, may reduce viscosity, and may enhance heat transfer.

Other optional additives includes anhydrous reinforcing and/or anhydrous extending fillers e.g. precipitated and ground silica, precipitated and ground calcium carbonate, treated silicas, glass beads, carbon black, graphite, carbon nanotubes, quartz, talc, chopped fibre such as chopped KEVLAR®, or a combination thereof, filler treating agents, stabilizers (e.g. a hydrosilylation cure stabilizer, a heat stabilizer, or a UV stabilizer), adhesion promoters, a surfactant, a flux agent, an acid acceptor, a hydrosilylation inhibitor and/or an anti-corrosion additives and a combination thereof. The filler can also be a siloxane resin comprising $R_3SiO_{1/2}$ units and $SiO_{4/2}$ units, where R is a hydroxyl or a hydrocarbon radical bound directly or via an oxygen atom to the silicon atom.

Filler Treating Agent

The thermally conductive filler and/or the anhydrous reinforcing and/or extending filler if present, may optionally be surface treated with a treating agent. Treating agents and treating methods are known in the art, see for example, U.S. Pat. No. 6,169,142 (col. 4, line 42 to col. 5, line 2). The surface treatment of the filler(s) is typically performed, for example with a fatty acid or a fatty acid ester such as a stearate, or with organosilanes, organosiloxanes, or organosilazanes such as hexaalkyl disilazane or short chain siloxane diols. Generally the surface treatment renders the filler(s) hydrophobic and therefore easier to handle and obtain a homogeneous mixture with the other components in the composition.

Adhesion Promoter

Suitable adhesion promoters may comprise alkoxysilanes of the formula $R^{14}_q Si(OR^{15})_{(4-q)}$, where subscript q is 1, 2, or 3, alternatively q is 3. Each $R^{14}$ is independently a monovalent organofunctional group. $R^{14}$ can be an epoxy functional group such as glycidoxypropyl or (epoxycyclohexyl)ethyl, an amino functional group such as aminoethylaminopropyl or aminopropyl, a methacryloxypropyl, a mercapto functional group such as mercaptopropyl or an unsaturated organic group. Each $R^{15}$ is independently an unsubstituted, saturated hydrocarbon group of at least 1 carbon atom. $R^{15}$ may have 1 to 4 carbon atoms, alternatively 1 to 2 carbon atoms. $R^{15}$ is exemplified by methyl, ethyl, n-propyl, and iso-propyl.

Examples of suitable adhesion promoters include glycidoxypropyltrimethoxysilane and a combination of glycidoxypropyltrimethoxysilane with an aluminium chelate or zirconium chelate. Examples of adhesion promoters for hydrosilylation curable compositions may be found in U.S. Pat. Nos. 4,087,585 and 5,194,649. The curable composition may comprise 0.01% to 1% of adhesion promoter based on the weight of the composition. Preferably, the speed of hydrolysis of the adhesion promoter should be lower than the speed of hydrolysis of the cross-linker in order to favour diffusion of the molecule towards the substrate rather than its incorporation in the product network.

Suitable surfactants include silicone polyethers, ethylene oxide polymers, propylene oxide polymers, copolymers of ethylene oxide and propylene oxide, other non-ionic surfactants, and combinations thereof. The composition may comprise up to 0.05% of the surfactant based on the weight of the composition.

Flux Agent

The composition may comprise up to 2% of a flux agent based on the weight of the composition. Molecules containing chemically active functional groups such as carboxylic acid and amines can be used as flux agents. Such flux agents can include aliphatic acids such as succinic acid, abietic acid, oleic acid, and adipic acid; aromatic acids such as benzoic acids; aliphatic amines and their derivatives, such as triethanolamine, hydrochloride salts of amines, and hydrobromide salts of amines. Flux agents are known in the art and are commercially available.

Acid Acceptor

Suitable acid acceptors include magnesium oxide, calcium oxide, and combinations thereof. The composition may comprise up to 2% of Acid Acceptor based on the weight of the composition, if appropriate.

Anti corrosion additives, such as nitrogen/sulphur containing heterocyclic compounds containing a triazole structure, a thiadiazole structure, a benzotriazole structure, a mercaptothiozole structure, a mercaptobenzothiazole structure or a benzimidazole structure.

In one embodiment of the invention the composition used to cure the gel is a mixture of a condensation curable polymer, cross-linker and catalyst as described above in combination with a hydrosilylation curable polymer together with a suitable cross-linker and catalyst. Any suitable polymer curable via a hydrosilylation reaction pathway may be utilized. Typically the polymer is a polydialkyl siloxane or polyalkylphenyl siloxane having terminal groups containing one or more unsaturated groups (e.g. alkenyl terminated e.g. ethenyl terminated, propenyl terminated, allyl terminated ($CH_2$=$CHCH_2$—)) or terminated with acrylic or alkylacrylic such as $CH_2$=$C(CH_3)$—$CH_2$— groups Representative, non-limiting examples of the alkenyl groups are shown by the following structures; $H_2C$=$CH$—, $H_2C$=$CHCH_2$—, $H_2C$=$C(CH_3)CH_2$—, $H_2C$=$CHCH_2CH_2$—, $H_2C$=$CHCH_2CH_2CH_2$—, and $H_2C$=$CHCH_2CH_2CH_2CH_2$—. Representative, non-limiting examples of alkynyl groups are shown by the following structures; $HC$≡$C$—, $HC$≡$CCH_2$—, $HC$≡$CC(CH_3)_2$—, $HC$≡$CC(CH_3)_2CH_2$— Alternatively, the unsaturated organic group can be an organofunctional hydrocarbon such as an acrylate, methacrylate and the like such as alkenyl and/or alkynyl groups. Alkenyl groups are particularly preferred. The hydrosilylation curable polymer may therefore be further defined as an alkenyldialkylsilyl end-blocked polydialkylsiloxane which may itself be further defined as vinyldimethylsilyl end-blocked polydimethylsiloxane. Alternatively The polymer may be further defined as a dimethylpolysiloxane capped at one or both molecular terminals with dimethylvinylsiloxy groups; a dimethylpolysiloxane capped at one or both molecular terminals with methylphenylvinylsiloxy groups; a copolymer of a methylphenylsiloxane and a dimethylsiloxane capped at both one or both molecular terminals with dimethylvinylsiloxy groups; a copolymer of diphenylsiloxane and dimethylsiloxane capped at one or both molecular terminals with dimethylvinylsiloxy groups, a copolymer of a methylvinylsiloxane and a dimethylsiloxane capped at one or both molecular terminals with dimethylvinylsiloxy groups; a copolymer of a methylvinylsiloxane and a dimethylsiloxane capped at one or both molecular terminals with dimethylvinylsiloxy groups; a methyl (3,3,3-trifluoropropyl) polysiloxane capped at one or both molecular terminals with dimethylvinylsiloxy groups; a copolymer of a methyl (3,3, 3-trifluoropropyl) siloxane and a dimethylsiloxane capped at one or both molecular terminals with dimethylvinylsiloxy groups; a copolymer of a methylvinylsiloxane and a dimethylsiloxane capped at one or both molecular terminals with silanol groups; a copolymer of a methylvinylsiloxane, a methylphenylsiloxane, and a dimethylsiloxane capped at one or both molecular terminals with silanol groups; or an organosiloxane copolymer composed of siloxane units represented by the following formulae: $(CH_3)_3SiO_{1/2}$, $(CH_3)_2(CH_2$=$CH)SiO_{1/2}$, $CH_3SiO_{3/2}$, $(CH_3)_2SiO_{2/2}$, $CH_3PhSiO_{2/2}$ and $Ph_2SiO_{2/2}$.

Hydrosilylation Cross-Linker

The hydrosilylation cross-linker has an average of at least 2 silicon-bonded hydrogen atoms per molecule and may be further defined as, or include, a silane or a siloxane, such as a polyorganosiloxane. In various embodiments, the hydrosilylation cross-linker may include more than 2, 3, or even more than 3, silicon-bonded hydrogen atoms per molecule. The hydrosilylation cross-linker may have a linear, a branched, or a partially branched linear, cyclic, dendrite, or resinous molecular structure. The silicon-bonded hydrogen atoms may be terminal or pendant. Alternatively, the hydrosilylation cross-linker may include both terminal and pendant silicon-bonded hydrogen atoms.

In addition to the silicon-bonded hydrogen atoms, the hydrosilylation cross-linker may also include monovalent hydrocarbon groups which do not contain unsaturated aliphatic bonds, such as methyl, ethyl, propyl, butyl, pentyl, hexyl, heptyl, octyl, decyl, undecyl, dodecyl, or similar alkyl groups; cyclopentyl, cyclohexyl, or similar cycloalkyl groups; phenyl, tolyl, xylyl, or similar aryl groups; benzyl, phenethyl, or similar aralkyl groups; or 3,3,3-trifluoropropyl, 3-chloropropyl, or similar halogenated alkyl group. Preferable are alkyl and aryl groups, in particular, methyl and phenyl groups.

The hydrosilylation cross-linker may also include siloxane units including, but not limited to, $HR^3{}_2SiO_{1/2}$, $R^3{}_3SiO_{1/2}$, $HR^3SiO_{2/2}$, $R^3{}_2SiO_{2/2}$, $R^3SiO_{3/2}$, and $SiO_{4/2}$ units. In the preceding formulae, each $R^3$ is independently selected from monovalent organic groups free of aliphatic unsaturation.

The hydrosilylation cross-linker may alternatively be further defined as a methylhydrogen polysiloxane capped at both molecular terminals with trimethylsiloxy groups; a copolymer of a methylhydrogensiloxane and a dimethylsiloxane capped at both molecular terminals with trimethylsiloxy groups; a dimethylpolysiloxane capped at both molecular terminals with dimethylhydrogensiloxy groups; a methylhydrogenpolysiloxane capped at one or both molecular terminals with dimethylhydrogensiloxy groups; a copolymer of a methylhydrogensiloxane and a dimethylsiloxane capped at both molecular terminals with dimethylhydrogensiloxy groups; a cyclic methylhydrogenpolysiloxane; and/or an organosiloxane composed of siloxane units represented by the following formulae: $(CH_3)_3SiO_{1/2}$, $(CH_3)_2HSiO_{1/2}$, and $SiO_{4/2}$; tetra(dimethylhydrogensiloxy) silane, or methyl-tri(dimethylhydrogensiloxy) silane.

It is also contemplated that the hydrosilylation cross-linker may be or include a combination of two or more organohydrogenpolysiloxanes that differ in at least one of the following properties: structure, average molecular weight, viscosity, siloxane units, and sequence. The hydrosilylation cross-linker may also include a silane. Dimethylhydrogensiloxy-terminated poly dimethylsiloxanes having relatively low degrees of polymerization (DP) (e.g., DP ranging from 3 to 50) are commonly referred to as chain extenders, and a portion of the hydrosilylation cross-linker may be or include a chain extender. In one embodiment, the hydrosilylation cross-linker is free of halogen atoms per molecule. In another embodiment, the hydrosilylation cross-linker includes one or more halogen atoms. It is contemplated that the gel, as a whole, may be free of halogen atoms or may include halogen atoms.

Hydrosilylation Catalyst

The hydrosilylation catalyst is not particularly limited and may be any known in the art. In one embodiment, the hydrosilylation catalyst includes a platinum group metal selected from platinum, rhodium, ruthenium, palladium, osmium or iridium, organometallic compounds thereof, or combinations thereof. In another embodiment, the hydrosilylation catalyst is further defined as a fine platinum metal powder, platinum black, platinum dichloride, platinum tetrachloride; chloroplatinic acid, alcohol-modified chloroplatinic acid, chloroplatinic acid hexahydrate; and complexes of such compounds, such as platinum complexes of olefins, platinum complexes of carbonyls, platinum complexes of alkenylsiloxanes, e.g. 1,3-divinyltetramethyldisiloxanes, platinum complexes of low molecular weight organopolysiloxanes, for example 1,3-diethenyl-1,1,3,3-tetramethyldisiloxane, complexes of chloroplatinic acid with β-diketones, complexes of chloroplatinic acid with olefins, and complexes of chloroplatinic acid with 1,3-divinyltetramethyldisiloxane.

Alternatively, the hydrosilylation catalyst may be further defined as a rhodium compound, such as those expressed by formulae: $RhX_3[(R^4)_2S]_3$; $(R^5_3P)_2Rh(CO)X$, $(R^5_3P)_2Rh(CO)H$, $Rh_2X_2Y_4$, $H_fRh_g(En)_hCl_i$, or $Rh[O(CO)R]_{3-j}(OH)_j$, wherein each X is independently a hydrogen atom, chlorine atom, bromine atom, or iodine atom, each Y is independently a methyl group, ethyl group, or a similar alkyl group, CO, $C_8H_{14}$, or 0.5 $C_8H_{12}$; each $R^4$ is independently a methyl, ethyl, propyl, or a similar alkyl group; a cycloheptyl, cyclohexyl, or a similar cycloalkyl group; or a phenyl, xylyl or a similar aryl group; each $R^5$ is independently a methyl group, ethyl group, or a similar alkyl group; phenyl, tolyl, xylyl, or a similar aryl group; methoxy, ethoxy, or a similar alkoxy group, wherein each "En" is ethylene, propylene, butene, hexene, or a similar olefin; subscript "f" is 0 or 1; subscript "g" is 1 or 2; subscript "h" is an integer from 1 to 4; subscript "i" is 2, 3, or 4; and subscript "j" is 0 or 1. Particularly suitable but non-limiting examples of rhodium compounds are $RhCl(Ph_3P)_3$, $RhCl_3[S(C_4H_9)_2]_3$, $[Rh(O_2CCH_3)_2]_2$, $Rh(OCCH_3)_3$, $Rh_2(C_8H_{15}O_2)_4$, $Rh(C_5H_7O_2)_3$, $Rh(C_5H_7O_2)(CO)_2$, and $Rh(CO)[Ph_3P](C_5H_7O_2)$.

The hydrosilylation catalyst may also be further defined as an iridium group compound represented by the following formulae: $Ir(OOCCH_3)_3$, $Ir(C_5H_7O_2)_3$, $[Ir(Z)(En)_2]_2$, or $[Ir(Z)(Dien)]_2$ wherein each "Z" is chlorine atom, bromine atom, iodine atom, or a methoxy group, ethoxy group, or a similar alkoxy group; each "En" is ethylene, propylene, butene, hexene, or a similar olefin; and "Dien" is (cyclooctadiene)tetrakis(triphenyl). The hydrosilylation catalyst may also be palladium, a mixture of palladium black and triphenylphosphine. The hydrosilylation catalyst and/or any of the aforementioned compounds may be microencapsulated in a resin matrix or coreshell type structure, or may be mixed and embedded in a thermoplastic organic resin powder, e.g. a methylmethacrylate resin, carbonate resin, polystyrene resin, silicone resin, or similar resin. Typically, the hydrosilylation catalyst is present/utilized in an amount of from 0.01 to 1,000 ppm, alternatively 0.1 to 500 ppm alternatively 1 to 500 ppm, alternatively 2 to 200, alternatively 5 to 150 ppm, based on the total weight of the hydrosilylation curable polymer and hydrosilylation cross-linker.

Optionally the dual cure embodiment may require the presence of a hydrosilylation stabilizer to prevent premature curing of the curable composition in the case of the embodiment having a dual cure composition including a hydrosilylation cure composition. In order to adjust speed of curing and to improve handling of the composition under industrial conditions, the composition may be further combined with an alkyne alcohol, enyne compound, benzotriazole, amines such as tetramethyl ethylenediamine, dialkyl fumarates, dialkenyl fumarates, dialkoxyalkyl fumarates, maleates such as diallyl maleate, and a combination thereof. Alternatively, the stabilizer may comprise an acetylenic alcohol. The following are specific examples of such compounds: such as 2-methyl-3-butyn-2-ol, 3-methyl-1-butyn-3-ol, 3,5-dimethyl-1-hexyn-3-ol, 2-phenyl-3-butyn-2-ol, 3-phenyl-1-butyn-3-ol, 1-ethynyl-1-cyclohexanol, 1,1-dimethyl-2-propenyl)oxy)trimethylsilane, methyl(tris(1,1-dimethyl-2-propynyloxy))silane, or similar acetylene-type compounds; 3-methyl-3-penten-1-yne, 3,5-dimethyl-3-hexen-1-yne, or similar en-yne compounds; Other additives may comprise hydrazine-based compounds, phosphines-based compounds, mercaptane-based compounds, cycloalkenylsiloxanes such as methylvinylcyclosiloxanes such as 1,3,5,7-tetramethyl-1,3,5,7-tetravinyl cyclotetrasiloxane, 1,3,5,7-tetramethyl-1,3,5,7-tetrahexenyl cyclotetrasiloxane, benzotriazole, or similar triazols. The content of such inhibitors in the hydrosilation-curable thermoconductive silicone elastomer composition may be within the range of 0.0001 to 5 parts by weight per 100 parts by weight of the hydrosilylation curable polymer.

There is also provided herein a method of making the gel as hereinbefore described whereby the aforementioned two parts of the composition are intermixed and cured. Subsequent to intermixing in one embodiment the condensation curable gel composition may be applied on to a substrate using a suitable dispenser such as for example curtain coaters, spray devices die coaters, dip coaters, extrusion coaters, knife coaters and screen coaters which upon gel formation is provides a coating on said substrate.

Gels in accordance with the above may be utilised in a wide variety of applications, including, for the sake of example as an encapsulant/pottant in an electronic article. The article may be a power electronic article e.g. an electronic component with gel disposed thereon such that the gel encapsulates, either partially or completely, the electronic component. Alternatively, the electronic article may include the electronic component and a first layer. The first layer is not particularly limited and may be a semiconductor, a dielectric, metal, plastic, carbon fibre mesh, metal foil, a perforated metal foil (mesh), a filled or unfilled plastic film (such as a polyamide sheet, a polyimide sheet, polyethylene naphthalate sheet, a polyethylene terephthalate polyester sheet, a polysulphone sheet, a polyether imide sheet, or a polyphenylene sulphide sheet), or a woven or nonwoven substrate (such as fibreglass cloth, fibreglass mesh, or aramid paper). Alternatively, the first layer may be further defined as a semiconductor and/or dielectric film. The gel may be sandwiched between the electronic component and the first layer, may be disposed on and in direct contact with the first layer, and/or on and in direct contact with the electronic component. If the gel is disposed on and in direct contact with the first layer, the gel may still be disposed on the electronic component but may include one or more layers or structures between the gel and the electronic component. The electronic component may be further defined as a chip, such as a silicon chip or a silicon carbide chip, one or more wires, one or more sensors, one or more electrodes, and the like. The electronic article is not particularly limited and may be, for the sake of example, defined as an insulated gate bipolar transistor (IGBT), a rectifier such as a Schottky diode, a PiN diode, a merged PiN/Schottky (MPS) rectifier and Junction barrier diode, a bipolar junction transistors (BJTs), a thyristor, a metal oxide field effect transistor (MOSFET), a high electron mobility transistor (HEMT), a static induction transistors (SIT), a power transistor, and the like. Alternatively the electronic article can be a power module, e.g. one of more of the aforementioned devices for power converters, inverters, boosters, traction controls, industrial motor controls, power distribution and transportation systems. The electronic article can alternatively be further defined as including one or more of the aforementioned devices.

The disclosure also provides a method of forming aforementioned electronic article. The method may include one or more of the aforementioned steps of forming the gel, the step of providing the gel, and/or the step of providing the electronic component. Typically, the method includes the curable compositions as hereinbefore described onto an electronic component and curing the composition to form a gel on the electronic component under the condition sufficient to form the gel without damaging the component. The gel may be formed on the electronic component. Alternatively, the gel may be formed apart from the electronic component and subsequently be disposed on the electronic component.

Alternatively, the silicone gel may be utilised in adhesive compositions for use as the skin-facing layer of a medical device or wound dressing. In addition to the silicone gel adhesive composition, the medical device or wound dressing contains an absorbable or porous substrate. The absorbable substrate may be any material known to those of skill in the art capable of at least partially absorbing the exudate from a wound. Absorbable substrates include, but are not limited to, the following materials: foams (e.g., polyurethane and/or polymer foams), synthetic sponges, natural sponges, silks, keratins (e.g., wool and/or camel hair), cellulosic fibres (e.g., wood pulp fibres, cotton fibres, hemp fibres, jute fibres, and/or flax fibres), rayon, acetates, acrylics, cellulose esters, modacrylics, polymers, super-absorbent polymers (e.g., polymers capable of absorbing approximately 10 times their weight or greater), polyamides, polyesters, polyolefins, polyvinyl alcohols, and/or other materials. Combinations of one or more of the above-listed materials may also be used as the absorbable or porous substrate.

The silicone gel as hereinbefore described may be incorporated in adhesive compositions for use as the skin-facing layer in various applications where suitable skin-facing adhesive materials are desired, e.g. in athletic apparel such as biking shorts and feminine hygiene products.

Other applications include the manufacturing of silicone adhesive tapes (e.g. polyurethane nonwoven/fabric with silicone gel on it), gel sheeting (e.g. polyurethane film with gel on it), wound dressings (e.g. polyurethane film or polyurethane foam with gel on it), bandages, adhesive strips, surgery drapes (e.g., polyethylene with gel on it), topical or transdermal patches, fragrance/cosmetics patches and the like. As most gels prepared by curing the compositions described in this invention are visually crystal clear, these materials can be used to seal, glue or protect materials in optical devices or for any other purposes linked to its transparency. Still further potential applications include protection for light emitting diodes, gels or elastomers for implants and prosthesis, shoe sole, elastomers for drug release applications, and in tire industry as an anti-puncture material or a self-sealing pneumatic rubber tire. A self-sealing pneumatic rubber tire with a sealing band adheringly attached in the circumferential direction on the inner side of the tire, radially within the tread, with the gel as herein before described applied on a carrier material. The invention also relates to a method for producing a self-sealing tire using a sealing band with a sealant applied on a carrier material, which sealing band is introduced into the tire and applied on the inner wall surface of the tire, running between the shoulder regions.

EXAMPLES

In a first embodiment wherein the gel is solely cured via a condensation pathway, a series of gels (examples 1 to 16) as herein described were prepared as a one part composition (to save lab time). It was identified that compositions of the type depicted in Examples 1-16 will in practice have to be sold in multiple part compositions because they were found to cure in the cartridge prior to intended use. Examples 17-19 provide examples of how the compositions need to be stored prior to use with a view to avoid curing in storage. The compositions in Examples 1 to 19 were unexpectedly found to be cured in bulk after only 2 to 3 hours, contrary to expectations. All viscosity values were measured at 23° C. using a Brookfield cone plate viscometer (RV DIII) adapting the cone plate and the speed according to the polymer viscosity. Each prepared composition was evaluated to determine penetration and softness, using the methods described below, in the Tables below:

Example 1

100 parts per weight of a hydroxydimethyl silyl terminated polydimethylsiloxane polymer having a viscosity at 23° C. of 2000 mPa·s (Brookfield cone plate viscometer (RV DIII) using a cone plate CP-52 at 20 rpm) was introduced into a dental container followed by 1 part by weight of methyltrimethoxysilane cross-linker per 100 parts by weight of the polymer. The resulting mixture was then stirred in a speedmixer for 30 seconds at a speed of 2000 rpm. Subsequently 0.08 parts of tetra n-butyl titanate per 100 parts by weight of the polymer was added and the final mixture was stirred again in the speedmixer for a further 30 seconds at a speed of 2000 rpm. The total weight of the mixture was 70 g. The mixture was poured in a 50 ml aluminium cup and cured at 23° C. in a Relative Humidity (RH) of 50%.

Example 2

The same method of preparation was utilised as described in Example 1 with the exception that 1 part of tetraethoxysilane per 100 parts by weight of the polymer was utilised as the cross-linker.

Example 3

The same method of preparation was utilised as described in Example 1 with the exception that 0.4 parts of 1,6-bis (trimethoxysilyl)hexane per 100 parts by weight of the polymer was utilised as the cross-linker.

Example 4

The same method of preparation was utilised as described in Example 1 with the exception that 0.5 parts of 1,6-bis (trimethoxysilyl)hexane per 100 parts by weight of the polymer was utilised as the cross-linker.

Example 5

The same method of preparation was utilised as described in Example 1 with the exception that 0.7 parts of 1,6-bis (trimethoxysilyl)hexane per 100 parts by weight of the polymer was utilised as the cross-linker.

Example 6

The same method of preparation was utilised as described in Example 1 with the exception that 1 part of 1,6-bis (trimethoxysilyl)hexane per 100 parts by weight of the polymer was utilised as the cross-linker.

Example 7

The same method of preparation was utilised as described in Example 1 with the exception that 1 part of methyltrioximino silane per 100 parts by weight of the polymer was utilised as the cross-linker.

Example 8

The same method of preparation was utilised as described in Example 1 with the exception that 1 part of a 50/50 by weight mixture of methyl triacetoxysilane and ethyl triacetoxysilane per 100 parts by weight of the polymer was utilised as the cross-linker.

Example 9

100 parts per weight of a hydroxydimethyl silyl terminated polydimethyl siloxane polymer having a viscosity at 23° C. of 2000 mPa·s (Brookfield cone plate viscometer (RV DIII) using a cone plate CP-52 at 20 rpm) was introduced into a dental container followed by 0.8 part of methyltrimethoxysilane cross-linker per 100 parts by weight of the polymer. The resulting mixture was then stirred in a speedmixer for 30 seconds at a speed of 2000 rpm. Subsequently 0.02 parts of tetra n-butyl titanate per 100 parts by weight of the polymer was added and the final mixture was stirred again in the speedmixer for a further 30 seconds at a speed of 2000 rpm. The total weight of the mixture was 184.69 g. The mixture was poured in a 50 ml aluminium cup and cured at 23° C. in an RH of 50%.

Example 10

100 parts per weight (e.g. 150 g) of a hydroxydimethyl silyl terminated polydimethyl siloxane polymer having a viscosity at 23° C. of 2000 mPa·s (Brookfield cone plate viscometer (RV DIII) using a cone plate CP-52 at 20 rpm) was introduced into a dental container followed by 0.77 parts (e.g. 1.15 g) of tetraethoxysilane cross-linker per 100 parts by weight of the polymer. The resulting mixture was then stirred in a speedmixer for 30 seconds at a speed of 2000 rpm. Subsequently 0.02 parts of tetra n-butyl titanate (e.g. 0.30 g) per 100 parts by weight of the polymer was added and the final mixture was stirred again in the speedmixer for a further 30 seconds at a speed of 2000 rpm. The total weight of the mixture was 151.45 g. The mixture was poured in a 50 ml aluminium cup and cured at 23° C. in an RH of 50%.

Example 11

The same method of preparation was utilised as described in Example 9 with the exception that 0.6 parts of 1,6-bis(trimethoxysilyl)hexane per 100 parts by weight of the polymer was utilised as the cross-linker and 0.2 parts of tetra t-butyl titanate was added and the weight of the final mixture was 218.3 g

Example 12

100 parts per weight of a hydroxydimethyl silyl terminated polydimethyl siloxane polymer having a viscosity at 23° C. of 4000 mPa·s (Brookfield cone plate viscometer (RV DIII) using a cone plate CP-52 at 20 rpm) was introduced into a dental container followed by 0.71 parts of 1,6-bis(trimethoxysilyl)hexane cross-linker per 100 parts by weight of the polymer. The resulting mixture was then stirred in a speedmixer for 30 seconds at a speed of 2000 rpm. Subsequently 0.15 parts of tetra n-butyl titanate per 100 parts by weight of the polymer was added and the final mixture was stirred again in the speedmixer for a further 30 seconds at a speed of 2000 rpm. The total weight of the mixture was 100.86 g. The mixture was poured in a 50 ml aluminium cup and cured at 23° C. in an RH of 50%.

Example 13

100 parts per weight of a hydroxydimethyl silyl terminated polydimethyl siloxane polymer having a viscosity at 23° C. of 13,500 mPa·s (Brookfield cone plate viscometer (RV DIII) using a cone plate CP-52 at 5 rpm) was introduced into a dental container followed by 0.47 parts of 1,6-bis(trimethoxysilyl)hexane cross-linker per 100 parts by weight of the polymer. The resulting mixture was then stirred in a speedmixer for 30 seconds at a speed of 2000 rpm. Subsequently 0.10 parts of tetra n-butyl titanate per 100 parts by weight of the polymer was added and the final mixture was stirred again in the speedmixer for a further 30 seconds at a speed of 2000 rpm. The total weight of the mixture was 100.57 g. The mixture was poured in a 50 ml aluminium cup and cured at 23° C. in an RH of 50%.

Example 14

100 parts per weight of a hydroxydimethyl silyl terminated polydimethyl siloxane polymer having a viscosity at 23° C. of 50,000 mPa·s (Brookfield cone plate viscometer (RV DIII) using a cone plate CP-51 at 0.5 rpm) was introduced into a dental container followed by 0.33 part of 1,6-bis(trimethoxysilyl)hexane cross-linker per 100 parts by weight of the polymer. The resulting mixture was then stirred in a speedmixer for 30 seconds at a speed of 2000 rpm. Subsequently 0.07 parts of tetra n-butyl titanate per 100 parts by weight of the polymer was added and the final mixture was stirred again in the speedmixer for a further 30 seconds at a speed of 2000 rpm. The total weight of the mixture was 100.40 g. The mixture was poured in a 50 ml aluminium cup and cured at 23° C. in an RH of 50%.

Example 15

100 parts per weight of a hydroxydimethyl silyl terminated polydimethyl siloxane polymer having a viscosity at 23° C. of 2000 mPa·s (Brookfield cone plate viscometer (RV DIII using a cone plate CP-52 at 20 rpm) was introduced into a dental container followed by 0.7 part of 1,6-bis(trimethoxysilyl)hexane cross-linker per 100 parts by weight of the polymer. The resulting mixture was then stirred in a speedmixer for 30 seconds at a speed of 2000 rpm. Subsequently 0.25 parts of titanium diisopropoxide bis(ethylacetoacetate) per 100 parts by weight of the polymer was added and the final mixture was stirred again in the speedmixer for a further 30 seconds at a speed of 2000 rpm. The total weight of the mixture was 100.95 g. The mixture was poured in a 50 ml aluminium cup and cured at 23° C. in an RH of 50%. The cured product is yellowing over time.

Example 16

100 parts per weight of a hydroxydimethyl silyl terminated polydimethylsiloxane polymer partially trimethylsilyl terminated exhibiting viscosity at 23° C. of about 12,500 mPa·s (Brookfield cone plate viscometer (RV DIII) using a cone plate CP-52 at 5 rpm) was introduced into a dental container followed by 0.37 part of 1,6-bis(trimethoxysilyl)hexane cross-linker per 100 parts by weight of the polymer. The resulting mixture was then stirred in a speedmixer for 30 seconds at a speed of 2000 rpm. Subsequently 0.08 parts of tetra t-butyl titanate per 100 parts by weight of the polymer was added and the final mixture was stirred again in the speedmixer for a further 30 seconds at a speed of 2000 rpm. The total weight of the mixture was 100.45 g. The mixture was poured in a 50 ml aluminium cup and cured at 23° C. in an RH of 50%.

Example 17

Preparation of a Two Part Mixture 100 parts per weight of a hydroxydimethyl silyl terminated polydimethylsiloxane polymer having a viscosity at 23° C. of 50,000 mPa·s (Brookfield cone plate viscometer (RV DIII) using a cone plate CP-51 at 0.5 rpm) was introduced into a dental container followed by 0.62 parts of 1,6-bis(trimethoxysilyl)hexane cross-linker per 100 parts by weight of the polymer. The resulting mixture was then stirred in a speedmixer for 30 seconds at a speed of 2000 rpm and filled in a 300 ml cartridge as part A of a two part composition.

100 parts per weight of a hydroxydimethyl silyl terminated polydimethylsiloxane polymer having a viscosity at 23° C. of 50,000 mPa·s (Brookfield cone plate viscometer (RV DIII) using a cone plate CP-51 at 0.5 rpm) was introduced into a dental container followed by 0.08 parts of tetra n-butyl titanate per 100 parts by weight of the polymer. The resulting mixture was then stirred in a speedmixer for 30 seconds at a speed of 2000 rpm and filled in a 300 ml cartridge as part B of the two part composition.

A mixture 1:1 in weight of part A and Part B were mixed in a speedmixer for 30 seconds at a speed of 2000 rpm. The mixture was poured in a 50 ml aluminium cup and cured at 23° C. in an RH of 50%.

Example 18

Preparation of a Two Part Mixture 100 parts per weight of a hydroxydimethyl silyl terminated polydimethylsiloxane polymer having a viscosity at 23° C. of 13,500 mPa·s (Brookfield cone plate viscometer (RV DIII) using a cone plate CP-52 at 5 rpm) was introduced into a dental container followed by 0.94 parts of 1,6-bis(trimethoxysilyl)hexane cross-linker per 100 parts by weight of the polymer. The resulting mixture was then stirred in a speedmixer for 30 seconds at a speed of 2000 rpm and filled in a 300 ml cartridge as part A of a two part composition.

100 parts per weight of a hydroxydimethyl silyl terminated polydimethylsiloxane polymer having a viscosity at 23° C. of 13,500 mPa·s (Brookfield cone plate viscometer (RV DIII) using a cone plate CP-52 at 5 rpm) was introduced into a dental container followed by 0.16 parts of tetra n-butyl titanate per 100 parts by weight of the polymer. The resulting mixture was then stirred in a speedmixer for 30 seconds at a speed of 2000 rpm and filled in a 300 ml cartridge as part B of the two part composition.

A mixture 1:1 in weight of part A and Part B were mixed in a speedmixer for 30 seconds at a speed of 2000 rpm. The mixture was poured in a 50 ml aluminium cup and cured at 23° C. in an RH of 50%.

Example 19

Preparation of a Two Part Mixture 100 parts per weight of a trimethoxysilyl terminated polydimethylsiloxane polymer having a viscosity at 23° C. of 56,000 mPa·s (Brookfield cone plate viscometer (RV DIII) using a cone plate CP-52 at 5 rpm) was introduced into a dental container 0.2 parts of tetra n-butyl titanate per 100 parts by weight of the polymer. The resulting mixture was then stirred in a speedmixer for 30 seconds at a speed of 2000 rpm and filled in a 300 ml cartridge as part A of a two part composition. The aforementioned trimethoxysilyl terminated polydimethylsiloxane polymer functions in this example as the cross-linker.

100 parts per weight of a hydroxydimethyl silyl terminated polydimethylsiloxane polymer having a viscosity at 23° C. of 50,000 mPa·s (Brookfield cone plate viscometer (RV DIII) using a cone plate CP-52 at 5 rpm) was introduced in a 300 ml cartridge as part B of the two part composition.

A mixture 1:5 in weight of part A and Part B were mixed in a speedmixer for 30 seconds at a speed of 2000 rpm. The mixture was poured in a 50 ml aluminium cup and cured at 23° C. in an RH of 50%.

A series of comparative compositions were also prepared as described below:

Comparative Example 1

100 parts per weight of a hydroxydimethyl silyl terminated polydimethylsiloxane polymer having a viscosity at 23° C. of 2000 mPa·s (Brookfield cone plate viscometer (RV DIII) using a cone plate CP-52 at 20 rpm) was introduced into a dental container followed by 0.5 part of methyltrimethoxysilane cross-linker per 100 parts by weight of the polymer. The resulting mixture was then stirred in a speedmixer for 30 seconds at a speed of 2000 rpm. Subsequently 0.08 parts of tetra n-butyl titanate per 100 parts by weight of the polymer was added and the final mixture was stirred again in the speedmixer for a further 30 seconds at a speed of 2000 rpm. The total weight of the mixture was 70 g. The mixture was poured in a 50 ml aluminium cup and cured at 23° C. in a Relative Humidity (RH) of 50%.

Comparative Example 2

The same method of preparation was utilised as described in Comparative Example 1 with the exception that 0.5 part of tetraethoxysilane per 100 parts by weight of the polymer was utilised as the cross-linker.

Comparative Example 3

The same method of preparation was utilised as described in Comparative Example 1 with the exception that 2.5 part of methyltrimethoxysilane per 100 parts by weight of the polymer was utilised as the cross-linker.

Comparative Example 4

The same method of preparation was utilised as described in Comparative Example 1 with the exception that 2.5 part of tetraethoxysilane per 100 parts by weight of the polymer was utilised as the cross-linker.

Comparative Example 5

The same method of preparation was utilised as described in Comparative Example 1 with the exception that 2.5 part of 1,6-bis(trimethoxysilyl)hexane per 100 parts by weight of the polymer was utilised as the cross-linker.

Comparative Example 6

The same method of preparation was utilised as described in Comparative Example 1 with the exception that 0.5 part of methyltrioximino silane per 100 parts by weight of the polymer was utilised as the cross-linker.

Comparative Example 7

The same method of preparation was utilised as described in Comparative Example 1 with the exception that 0.5 part of a 50/50 by weight mixture of methyl triacetoxysilane and ethyl triacetoxysilane per 100 parts by weight of the polymer was utilised as the cross-linker.

Comparative Example 8

100 parts per weight of a hydroxydimethyl silyl terminated polydimethylsiloxane polymer having a viscosity at 23° C. of 2000 mPa·s (Brookfield cone plate viscometer (RV DIII) using a cone plate CP-52 at 20 rpm) was introduced into a dental container followed by 0.5 part of 1,6-bis(trimethoxysilyl)hexane cross-linker per 100 parts by weight of the polymer. The resulting mixture was then stirred in a speedmixer for 30 seconds at a speed of 2000 rpm. Subsequently 0.04 parts of tetra n-butyl titanate per 100 parts by weight of the polymer was added and the final mixture was stirred again in the speedmixer for a further 30 seconds at a speed of 2000 rpm. The total weight of the mixture was set to 70 g. The mixture was poured in a 50 ml aluminium cup and cured at 23° C. in an RH of 50%.

Comparative Example 9

100 parts per weight of a hydroxydimethyl silyl terminated polydimethylsiloxane polymer having a viscosity at 23° C. of 2000 mPa·s (Brookfield cone plate viscometer (RV DIII) using a cone plate CP-52 at 20 rpm) was introduced into a dental container followed by 0.5 part of 1,6-bis(trimethoxysilyl)hexane cross-linker per 100 parts by weight of the polymer. The resulting mixture was then stirred in a speedmixer for 30 seconds at a speed of 2000 rpm. Subsequently 0.08 parts of dimethyl tin neodecanoate per 100 parts by weight of the polymer was added and the final mixture was stirred again in the speedmixer for a further 30 seconds at a speed of 2000 rpm. The total weight of the mixture was set to 70 g. The mixture was poured in a 50 ml aluminium cup and cured at 23° C. in an RH of 50%.

Comparative Example 10

100 parts per weight of a hydroxydimethyl silyl terminated polydimethylsiloxane polymer having a viscosity at 23° C. of 2000 mPa·s (Brookfield cone plate viscometer (RV DIII) using a cone plate CP-52 at 20 rpm) was introduced into a dental container followed by 0.5 part of 1,6-bis(trimethoxysilyl)hexane cross-linker per 100 parts by weight of the polymer. The resulting mixture was then stirred in a speedmixer for 30 seconds at a speed of 2000 rpm. Subsequently 0.08 parts of stannous octoate per 100 parts by weight of the polymer was added and the final mixture was stirred again in the speedmixer for a further 30 seconds at a speed of 2000 rpm. The total weight of the mixture was set to 70 g. The mixture was poured in a 50 ml aluminium cup and cured at 23° C. in an RH of 50%.

The level of cure was observed after 4 days (4 D) and 7 days (7 D) in the Tables below. Each sample cured was tested for Penetration and Hardness as described below: Penetration was measured after 3 days of cure at a temperature 23° C. and 50% relative humidity using a Universal Penetrometer with a total weight of about 19.5 g after 5 seconds of penetration of the head in the material (ASTM D217-10 (2010)). Results are provided in 1/10 mm and were measured a period of 7 days curing at 23° C. in an RH of 50%. Hardness was measured after 7 days (7 D) of cure at a temperature 23° C. and 50% relative humidity according to ASTM D2240-05(2010) in the Shore 00 scale. The results of the above are depicted in the following Tables:

TABLE 1a

|  | Ex. 1 | Ex. 2 | Ex. 3 | Ex. 4 | Ex. 5 | Ex. 6 |
| --- | --- | --- | --- | --- | --- | --- |
| Observation after 4D | CiD | CiD | CiD | CiD | CiD | CiD |
| Observation after 7D | CiD | CiD | CiD | CiD | CiD | CiD |
| Penetration (1/10 mm) after 7D cure | 25 | 0 | 92 | 61 | 7 | 0 |
| Hardness shore 00 after 7D cure | 0 | 18 | 0 | 0 | 0 | 13 |

CiD = cure in depth.

TABLE 1b

|  | Ex. 7 | Ex. 8 | Ex. 9 | Ex. 10 | Ex. 11 | Ex. 12 |
| --- | --- | --- | --- | --- | --- | --- |
| Observation after 4D | CiD | CiD | CiD | CiD | CiD | CiD |
| Observation after 7D | CiD | CiD | CiD | CiD | CiD | CiD |
| Penetration (1/10 mm) after 7D cure | 106 | 8 | 37 | 27 | 35 | 50 |
| Hardness shore 00 after 7D cure | 0 | 0 | 0 | 0 | 0 | 0 |

TABLE 1c

|  | Ex. 13 | Ex. 14 | Ex. 15 | Ex. 16 | Ex. 17 | Ex. 18 | Ex. 19 |
| --- | --- | --- | --- | --- | --- | --- | --- |
| Observation after 4D | CiD | CiD | CiD | CiD | CiD | CiD | CiD |
| Observation after 7D | CiD | CiD | CiD | CiD | CiD | CiD | CiD |
| Penetration (1/10 mm) after 7D cure | 50 | 62 | 0 | 107 | 47 | 7 | 31 |
| Hardness shore 00 after 7D cure | 0 | 0 | 9 | 0 | 0 | 0 | 0 |

TABLE 2a

| | Comparative Examples | | | | | |
|---|---|---|---|---|---|---|
| | C Ex. 1 | C Ex. 2 | C Ex. 3 | C Ex. 4 | C Ex. 5 | C Ex. 6 |
| Observation after 4D | No cure | No cure | Top skin cure not in bulk Cure like a one part elastomer | Top skin cure not in bulk Cure like a one part elastomer | Top skin cure not in bulk Cure like a one part elastomer | No cure |
| Observation after 7D | No cure | No cure | Cure in depth | Cure in depth | Cure in depth | No cure |
| Hardness shore 00 after 7D cure | Not measured | Not measured | 55 | 45 | 48 | Not measured |

TABLE 2b

| | Comparative Examples | | | |
|---|---|---|---|---|
| | C Ex 7 | C Ex 8 | C Ex 9 | C Ex 10 |
| Observation after 4D | No cure | No cure | No cure | Very gelly |
| Observation after 7D | No cure | Cured | Cured like a one part | Cured |
| Penetration (1/10 mm) after 7D cure | Not measured | 116 | 7 | 10 |

Comparative examples 1 and 2 may be directly compared to Examples 1 to 2 and it is noticeable that halving the amount of monosilane cross-linker resulted in no cure. Disilane cross-linkers appeared to be more efficient in the curing process than monosilane cross-linkers. Comparative examples 3 to 5 were provided to demonstrate that above a certain level of crosslinker there is no cure in bulk in the system but merely a skin cure that occurs through a moisture diffusion process as might usually be expected in condensation cure systems. Such composition could not be formulated to provide bulk cure like the typical two part moisture curing systems.

Comparative examples 6 and 7 should be compared with examples 7 and 8 and show the lower limit of crosslinker for oxime and acetoxy curing system respectively below which no cure is observed.

Comparative example 8 is to be compared to example 4 and provides the lower limit of titanate to be added in the system below which no cure is observed. At this level very slow cure is observed and the material is very soft. Comparative example 9 and 10 is comparable to example 4 and is showing that a tin IV catalyst is leading to a skin curing system and not to a bulk cure and the tin II is leading to a bulk cure but at a very low curing rate, which highlights that titanate catalyst works better for this system.

In a second embodiment there is provided a dual cure system in which there is provided a mixture of a condensation curable polymer and a hydrosilylation curable polymer, which are respectively cured using a condensation cross-linker and catalyst and using a hydrosilylation cross-linker and catalyst which results in cured end product being cured partially via a condensation pathway and partially via a hydrosilylation pathway Example 20

Preparation of a Two Part Dual Cure Mixture 50 parts per weight of a hydroxydimethyl silyl terminated polydimethylsiloxane polymer having a viscosity at 23° C. of 2000 mPa·s was introduced into a dental container followed by 50 parts per weight of a dimethylvinyl silyl terminated polydimethylsiloxane polymer per 50 parts by weight of hydroxydimethyl silyl terminated polydimethylsiloxane polymer having a viscosity at 23° C. of 450 mPa·s. The resulting mixture was then stirred in a speedmixer for 30 seconds at a speed of 2000 rpm. 0.5 parts per weight of 1,6-bis(trimethoxysilyl)hexane cross-linker per 100 parts by weight of the total polymer weight was introduced into the mixture and the resulting mixture was again stirred in a speedmixer for 30 seconds at a speed of 2000 rpm. 0.9 parts per weight of a trimethylsiloxy-terminated polydiorganosiloxane having an average of five methylhydrogensiloxane units and three dimethylsiloxane units per molecule with a silicon-bonded hydrogen atom content of about 0.7 to 0.8 weight percent was then introduced and the resulting mixture was again stirred in a speedmixer for 30 seconds at a speed of 2000 rpm. The final composition was filled in a 300 ml cartridge as part A of a two part composition.

50 parts per weight of a silanol terminated polydimethylsiloxane polymer exhibiting a viscosity at 23° C. of about 2,000 mPa·s has been added in a dental container followed by the addition of 50 parts per weight of a vinyl terminated polydimethylsiloxane polymer exhibiting a viscosity at 23° C. of about 450 mPa·s per 50 parts per weight of a silanol terminated polydimethylsiloxane polymer. The mixture was then mixed in a speedmixer for 30 seconds at a speed of 2000 rpm. Then 0.016 parts per weight of platinum(0)-1,3-divinyl-1,1,3,3-tetramethyldisiloxane has been added in the mixture and mixed in a speedmixer for 30 seconds at a speed of 2000 rpm. Finally, 0.08 parts per weight of tetra t-butyl titanate was added in the mixture and then mixed in a speedmixer for 30 seconds at a speed of 2000 rpm and filled in a 300 ml cartridge as part B.

50 parts per weight of a hydroxydimethyl silyl terminated polydimethylsiloxane polymer having a viscosity at 23° C. of 13,500 mPa·s was introduced into a dental container followed by 50 parts per weight of a dimethylvinyl silyl terminated polydimethylsiloxane polymer per 50 parts, per weight of the hydroxydimethyl silyl terminated polydimethylsiloxane polymer, having a viscosity at 23° C. of 450 mPa·s. The resulting mixture was then stirred in a speedmixer for 30 seconds at a speed of 2000 rpm. 0.016 parts per weight of the total polymer weight in Part B Platinum(0)-1,3-divinyl-1,1,3,3-tetramethyldisiloxane was added in the mixture with the resulting mixture being mixed in a speedmixer for 30 seconds at a speed of 2000 rpm. Finally, 0.08 parts per weight of tetra t-butyl titanate was added and the final mixture was also mixed in a speedmixer for 30 seconds at a speed of 2000 rpm and subsequently then filled in a 300 ml cartridge as part B of the two part composition.

A mixture 1:1 in weight of part A and Part B were mixed in a speedmixer for 30 seconds at a speed of 2000 rpm. The mixture was poured in a 50 ml aluminium cup and cured at 23° C. in an RH of 50%.

The resulting cured material was noted to be cured in bulk in about 12 minutes and after 7 days of cure had a hardness of Shore 00 (measured as described above) of 40.

The invention claimed is:

1. A medical application comprising a gel, wherein the gel is the reaction product of a condensation curable gel composition, the composition comprising:
 (i) at least one condensation curable silyl terminated polymer having at least one hydrolysable and/or hydroxyl functional group(s) per molecule;
 (ii) a cross-linker selected from the group of a monosilane or a disilane molecule which contains at least two hydrolysable groups per molecule; and
 (iii) a condensation catalyst selected from the group of titanates, zirconates or tin (II);
  wherein the molar ratio of hydroxyl and/or hydrolysable group(s) in polymer (i) to hydrolysable groups from component (ii) is between 0.5:1 and 1:1 using a monosilane cross-linker or 0.75:1 to 3:1 using disilanes;
  wherein the titanates and zirconates comprise M-OR functional groups where M is titanium or zirconium and R is an aliphatic hydrocarbon group; and
  wherein the molar ratio of M-OR functional groups to the hydroxyl and/or hydrolysable group(s) in polymer (i) is comprised between 0.01:1 and 0.5:1.

2. The medical application comprising the gel in accordance with claim 1, wherein prior to cure, the composition is stored in two parts having polymer (i) and cross-linker (ii) in one part, and polymer (i) and catalyst (iii) in the other part.

3. The medical application comprising the gel in accordance with claim 1, wherein prior to cure, the composition is stored in two parts having cross-linker (ii) in one part, and polymer (i) and catalyst (iii) in the other part.

4. The medical application comprising the gel in accordance with claim 1, wherein prior to cure, the composition is stored in two parts having a first polymer (i) and cross-linker (ii) in one part, and a second polymer (i) and catalyst (iii) in the other part.

5. The medical application comprising the gel in accordance with claim 1, wherein the molar ratio of M-OR functional groups to the hydroxyl and/or hydrolysable group(s) in polymer (i) is comprised between 0.02:1 and 0.2:1.

6. The medical application comprising the gel in accordance with claim 1, the composition further comprising a polymer curable by hydrosilylation, a hydrosilylation cross-linker, and a hydrosilylation catalyst.

7. The medical application comprising the gel in accordance with claim 1, wherein the cross-linker (ii) comprises the monosilane.

8. The medical application comprising the gel in accordance with claim 7, wherein the molar ratio of hydroxyl and/or hydrolysable group(s) in polymer (i) to hydrolysable groups from component (ii) is between 0.5:1 and 0.75:1.

9. The medical application comprising the gel in accordance with claim 1, wherein the cross-linker (ii) comprises the disilane molecule.

10. The medical application comprising the gel in accordance with claim 9, wherein the molar ratio of hydroxyl and/or hydrolysable group(s) in polymer (i) to hydrolysable groups from component (ii) is between 0.75:1 to 1.5:1.

11. The medical application comprising the gel in accordance with claim 1, wherein:
 i) the polymer (i) has at least two hydrolysable and/or hydroxyl functional groups per molecule;
 ii) the cross-linker (ii) contains at least three hydrolysable groups per molecule; or
 iii) both i) and ii).

12. The medical application comprising the gel in accordance with claim 11, wherein the polymer (i) has at least two hydrolysable and/or hydroxyl functional groups per molecule.

13. The medical application comprising the gel in accordance with claim 11, wherein the cross-linker (ii) contains at least three hydrolysable groups per molecule.

14. The medical application comprising the gel in accordance with claim 1, wherein the gel is for drug delivery, the gel is for wound care, a soft skin adhesive comprises the gel, a transdermal patch comprises the gel, and/or the gel is for the controlled release of medicaments.

* * * * *